United States Patent
Hopeck et al.

[11] Patent Number: 5,913,243
[45] Date of Patent: Jun. 15, 1999

[54] ULTRASONIC TRANSDUCER FOR NONDESTRUCTIVE TESTING OF GENERATOR FIELD COILS OF DYNAMOELECTRIC MACHINES

[75] Inventors: James F. Hopeck, Mechanicville, N.Y.; Peter B. Nagy, Cincinnati, Ohio

[73] Assignee: General Electric Co., Schenectady, N.Y.

[21] Appl. No.: 08/941,200

[22] Filed: Sep. 30, 1997

[51] Int. Cl.⁶ .................................................. G01N 29/24
[52] U.S. Cl. ............................................................ 73/644
[58] Field of Search ........................... 73/644, 617, 625, 73/626, 628, 641

[56] References Cited

U.S. PATENT DOCUMENTS

| | | | |
|---|---|---|---|
| 3,937,068 | 2/1976 | Joy | 73/644 |
| 4,279,167 | 7/1981 | Erb et al. | 73/644 |
| 4,458,534 | 7/1984 | Kising | 73/644 |
| 4,615,218 | 10/1986 | Pagano | 73/639 |
| 4,794,930 | 1/1989 | Machida et al. | 73/644 |
| 5,050,436 | 9/1991 | Kunii et al. | 73/644 |
| 5,546,813 | 8/1996 | Hastings et al. | 73/861.29 |

*Primary Examiner*—Hezron Williams
*Assistant Examiner*—Rose M. Miller
*Attorney, Agent, or Firm*—Nixon & Vanderhye

[57] ABSTRACT

An ultrasonic transducer for use in nondestructive testing includes a multi-transducer array mounted on a wedge, the wedge including a surface substantially contoured to conform to a sensing surface to be tested. At least the surface is covered by a silicone rubber material cast as a tubular sleeve which has the following properties:

- tensile strength—600 psi
- tear strength—135 psi
- sound velocity—1,000 m/s
- density—1,200 kg/m³
- Shore A Durometer—16.

16 Claims, 4 Drawing Sheets

ULTRASONIC TRANSDUCER FOR NONDESTRUCTIVE TESTING OF GENERATOR FIELD COILS OF DYNAMOELECTRIC MACHINES

TECHNICAL FIELD

This invention relates to nondestructive ultrasonic testing of braze joints in generator field coils of dynamoelectric machines.

BACKGROUND

In an era of aging infrastructure, increasing environmental degradation, and fierce international competition for market share, nondestructive testing has become a financial and social necessity offering potentially enormous benefits. It is one of the primary vehicles companies rely on in their pursuit of ever higher product quality. Ultrasonic inspection based on very high frequency sound propagation in structural materials is probably the most widely used nondestructive testing method to detect lack of bond, porosity, internal cracking, corrosion, and other structural defects in welded and brazed joints.

The outstanding sensitivity of ultrasonic inspection for detecting material discontinuities is due to the large difference in elastic modulus between the structural material to be inspected and the air usually filling the discontinuities to be detected. The relative contrast between the elastic moduli of the reflecting layer $C_1$ and the surrounding host material C can be defined as follows.

$$\xi = \pi C/C_1.$$

For example, acoustic contrast is as high as $6.7 \times 10^6$ for an air-filled crack in steel, but only $3.5 \times 10^2$ for a water-filled crack. For thin reflective layers, the reflection coefficient can be approximated as:

$$R = \xi d/\lambda$$

where d denotes the thickness of the layer and $\lambda$ is the ultrasonic wavelength in the host material. For example, the acoustic wavelength in steel is approximately 2.2 mm at 2.5 MHz. Assuming a modest 10% threshold sensitivity, an extremely thin 0.3-Å-wide air gap or a somewhat wider but still impressive 0.6-micron-thick water-filled crack can be detected at this frequency.

This remarkable sensitivity to material discontinuities represents also the most severe limitation for ultrasonic nondestructive testing because of the requirement that good acoustic coupling be maintained between the transducer and the object to be inspected (the specimen) without the slightest discontinuity between them. This goal can be achieved on flat, smooth surfaces by using some kind of fluid coupling to fill the inevitable thin, typically sub-micron, gap between the transducer and the specimen. The same technique is much less effective on curved surfaces, however, where the width of the gap between the transducer and the specimen is inherently wider. The simplest curved surfaces are convex and concave cylindrical surfaces that can be relatively easily coupled by matching cylindrical wedges. FIGS. 1A–1D illustrates how special contoured transducer wedges polished to the exact radius of the specimens to be inspected can be used in axial or circumferential directions. Although such custom-made transducer wedges can improve coupling on curved surfaces by eliminating rocking and couplant build-up underneath the wedge, precise matching is often prevented by inevitable variations in the surface curvature of the specimens. This variation becomes especially crucial when large-aperture, e.g., multiple-element array, transducers are used in electronically scanned multi-channel systems.

Contoured transducer wedges also limit the operator's ability to freely align the transducer. On a flat surface, an angle-beam transducer can be translated in both the forward direction and sideways as well as rotated in the plane of the surface. As is readily apparent from FIGS. 1A–1D, contoured angle-beam transducers with cylindrical faces can also be translated both forward and sideways, but cannot be rotated as the radius of curvature is finite in one direction and infinite in the other.

The coupling problem is further exacerbated on double-curved surfaces. For example, thick plates and rods bent in one direction at a principal convex radius of curvature inherently assume a secondary concave curvature in the orthogonal direction due to the so-called Poisson effect as it is shown in FIG. 2. Such surfaces are very difficult to accurately match with precision contoured angle beam transducers of double-cylindrical faces, and the transducer cannot be laterally translated or rotated at all without losing contact between the wedge and the specimen. The inevitably larger surface gap requires the use of large amounts of high-viscosity couplants, but even this undesirable solution is rendered useless when the radius of curvature exhibits a significant variation from specimen to specimen.

In generator field coils of dynamoelectric machines, high quality braze joints are of paramount importance to maintain generator quality and integrity. The usual visual inspections method do not address the problem of hidden defects caused by operator error, improper cleanness, contamination of the joint area by oil, grease, varnish, etc. all prevalent in a heavy industrial environment. Other nondestructive testing methods, because of the very large size and weight of the fields, preclude their use. The double-curvature (discussed above) of the field coils also limits the standard single transducer ultrasonic method because it is time consuming, expensive and not suitable for a production environment.

One conventional technique for providing acoustic coupling on irregular, curved surfaces is to equip the transducer with an oil-filled rubber balloon or wheel that can easily conform to the exact shape of the specimen. However, in tough industrial environment the necessarily very thin rubber balloon often ruptures, spilling the oil couplant. This presents an unacceptable contamination risk in certain applications such as brazing and generator field winding operations, where any contamination, however minor, is totally unacceptable.

A solid rubber coupling would be more desirable in the applications discussed above. However, special low-attenuation rubbers have inherently high stiffness requiring relatively thick rubber cushions to conform to the irregular surface, and therefore the transmission loss is still significant. On the other hand, special low-stiffness rubbers are usually excellent sound absorbents therefore cannot be used as padding materials for ultrasonic coupling purposes. Thus, solid rubber coupling techniques improve sensitivity but are not completely satisfactory.

SUMMARY OF THE INVENTION

This invention seeks to allow a semi-skilled hourly employee to perform without disruption of production, a nondestructive braze joint test within one minute to assure that the generator field quality and integrity meets the highest possible standard. To this end, a silicone rubber material has been identified which has both low stiffness and low attenuation, and which is therefore an eminently suitable coupling material.

After experimenting with numerous silicone rubber compounds, we have identified Dow Corning® HS II high-strength moldmaking silicone rubber as the best commercial candidate for casting compliant, low-attenuation, solid coupling pads. One disadvantage with this material, however, is that, because it is a moldmaking substance, it does not stick to other materials, and cannot be permanently mounted on standard polymer wedges by adhesive means. Special mechanical fixtures can assure durability of the padded wedge but at the expense of increased acoustic scattering caused by the fixture. The resulting internal reverberations increase the internal noise of the probe and reduce its threshold sensitivity during inspection. In order to overcome these difficulties, the coupling material is cast as a tube-like, silicone rubber "sock" which relies solely on the outstanding strength and formability of the silicone rubber to keep the sock solidly in place on the transducer wedge without the need for special fixturing devices.

Thus, in one aspect, the present invention relates to an ultrasonic transducer for use in nondestructive testing comprising a multi-transducer array mounted on a wedge, the wedge including a coupling or sensing surface substantially contoured to conform to a surface to be tested wherein at least the coupling or sensing surface is covered by a solid silicone rubber material.

In another aspect, the invention relates to an ultrasonic transducer for use in nondestructive testing comprising a multi-transducer array mounted on a wedge, the wedge including a sensing surface substantially contoured to conform to a surface to be tested wherein at least part of the transducer and the sensing surface is covered by a silicone rubber sleeve.

Other objects and advantages of the invention will become apparent from the detailed description which follows.

DETAILED DESCRIPTION OF THE DRAWINGS

Figure 1A:
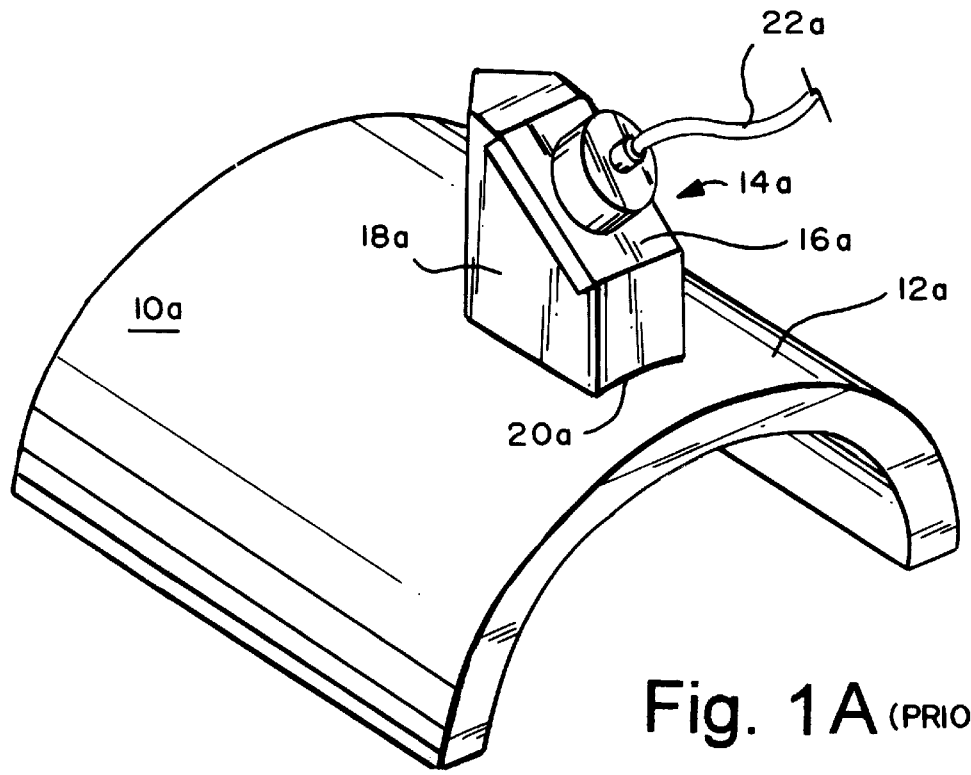
FIGS. 1A–1D illustrate various contoured angle-beam transducer wedges adapted for inspection of typical surface contours.

Referring initially to FIGS. 1A–1D, specially adapted contoured angle-beam wedges are illustrated in connection with typical contoured surfaces requiring inspection. In FIG. 1A, a test specimen $10_a$ is shown having an axially concave surface $12_a$ requiring inspection by an angle-beam wedge transducer $14_a$ The latter includes a transducer array $16_a$ mounted on a specially contoured wedge $18_a$. The latter includes a sensing surface $20_a$ which has been polished to substantially the exact radius of the specimen $10_a$. The transducer cable $22_a$ connects the unit to a suitable computer-controlled multiplexer.

Figure 1B:
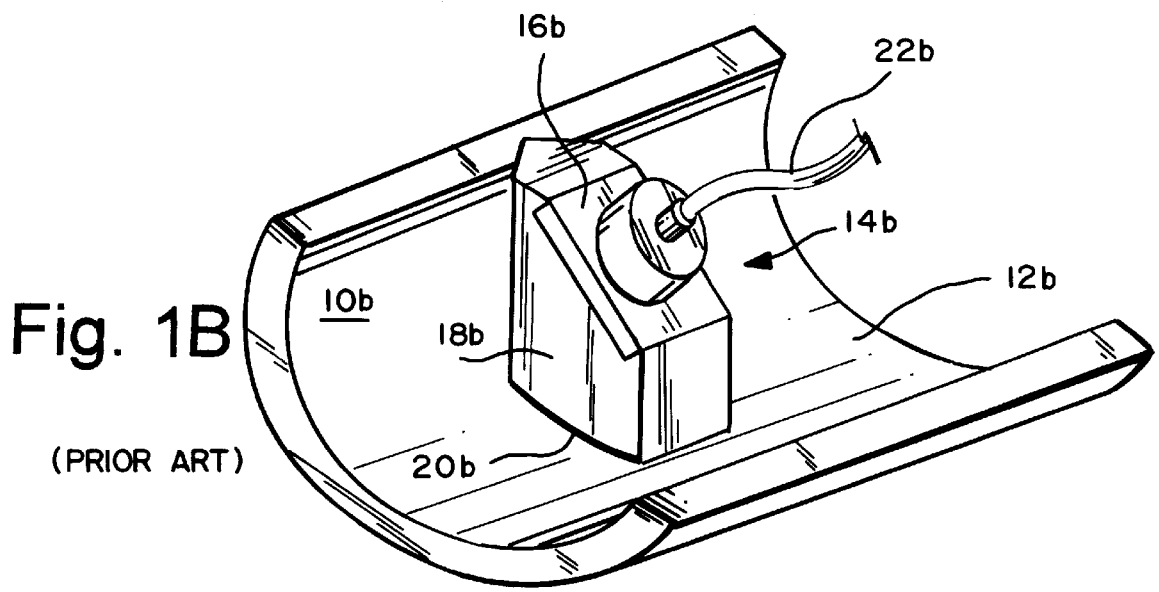

In FIG. 1B, the test specimen $10_b$ has an axially convex surface $12_b$ to be inspected by the angle-beam wedge $14_b$. In this instance, the coupling or sensing surface $20_b$ is polished to match the contour of the axially convex surface $12_b$.

Figure 1C:
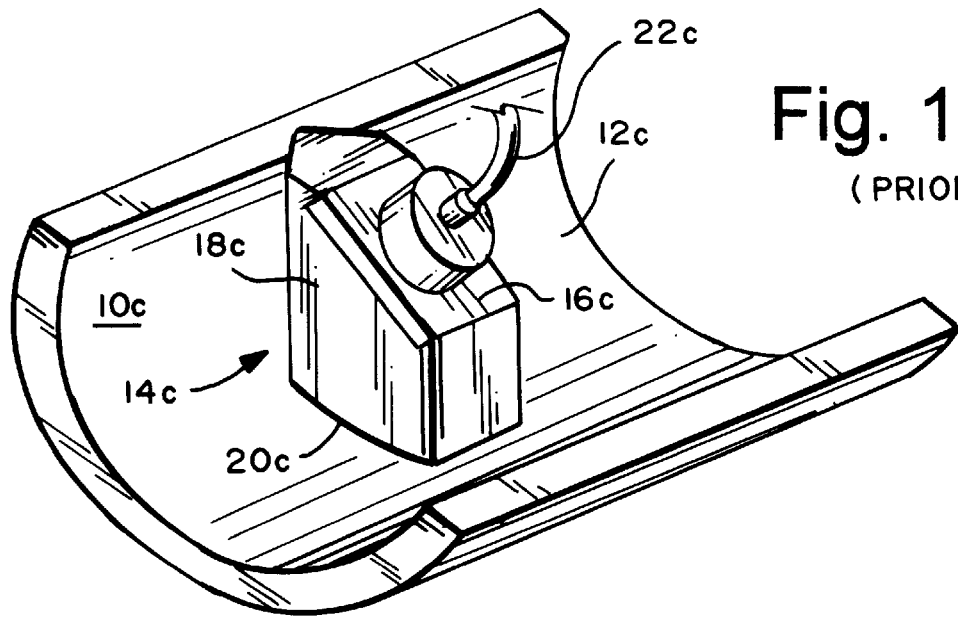

In FIG. 1C, the test specimen $10_c$ is formed with a circumferentially concave sensing surface $12_c$ and in this case, the angle-beam wedge $14_c$ is formed with a polished surface $20_c$, again matching the contour of the surface $12_c$.

Figure 1D:
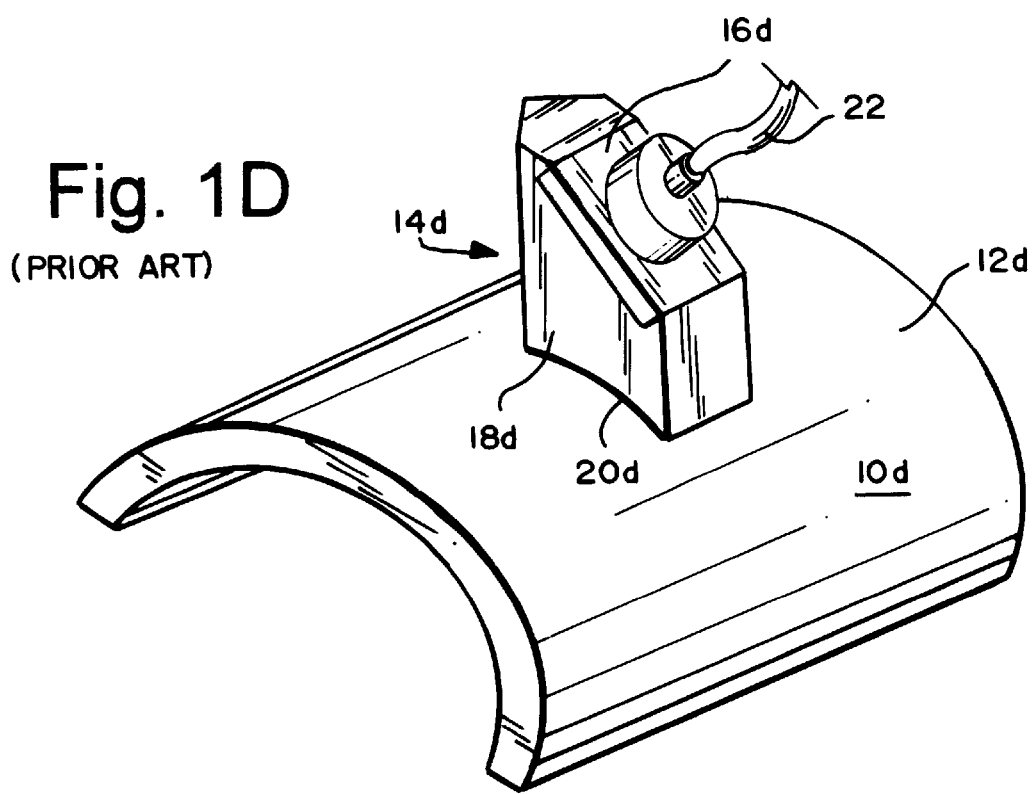

Similarly, in FIG. 1D, a circumferentially convex surface $12_d$ on the test specimen $10_d$ is inspected by the angle-beam wedge $14_d$ formed with a polished surface $20_d$ matching the contour of sensing surface $12_d$.

Figure 2:
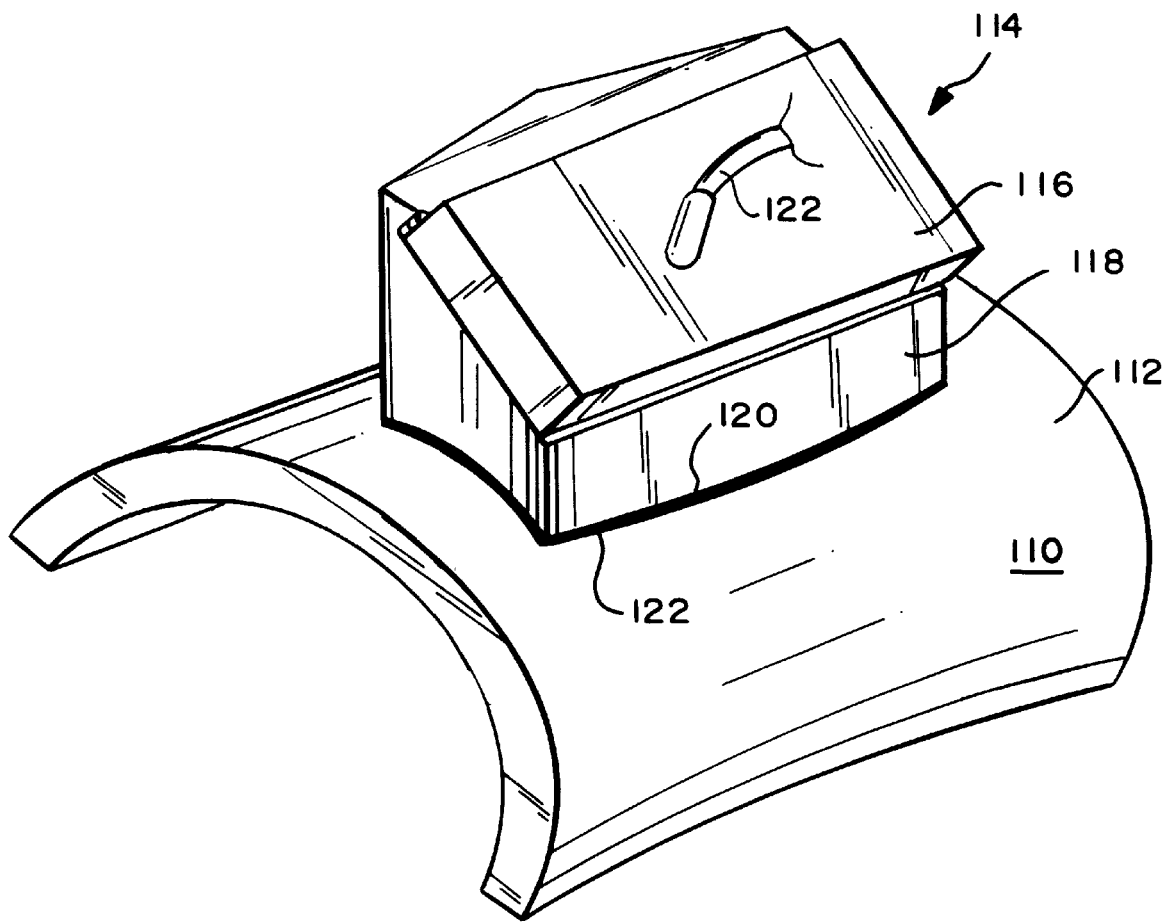
FIG. 2 is a perspective view of yet another conventional contoured angle-beam wedge located on a double curved surface.

In FIG. 2, a double curved contour is illustrated which is also found in field coils of dynamoelectric machines. Here, the test specimen 110 has an exterior surface 112 which is convex in a circumferential direction but concave in an axial direction, thus forming a double curvature which has been very difficult to accurately match with precision contoured angle-beam transducers. One such transducer is shown at 114 and includes a multi-transducer array 116. The wedge 118 has a sensing surface 120 which is covered by a solid rubber pad 124. However, even with the solid rubber pad 124, the inspection unit 114 cannot be laterally translated or rotated without losing contact between the transducer wedge 118 and the specimen 110.

Figure 3:
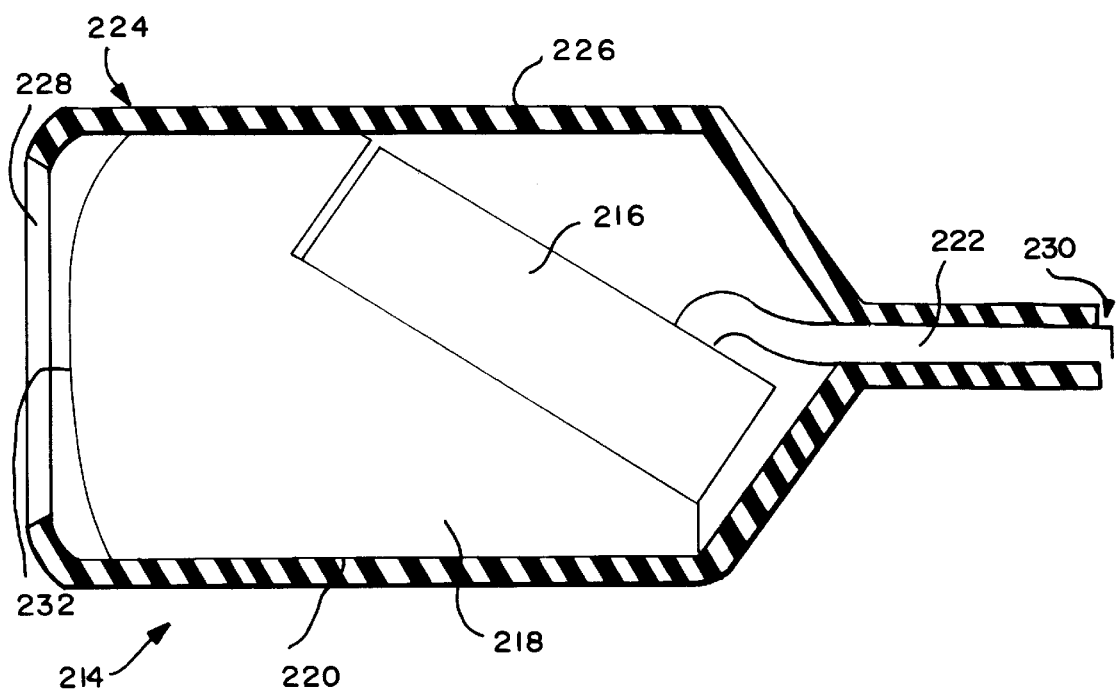
FIG. 3 is a side elevation, partly in section, of a multi-transducer array enclosed within a silicone rubber sock in accordance with an exemplary embodiment of this invention.

Turning now to FIG. 3, an ultrasonic transducer 214 in accordance with this invention includes an angle-beam transducer unit 216 mounted on a polymer wedge 218 (preferably Plexiglas®) having a lower contour surface 220. Unit 216 may include a special array of six 0.5"×1", 2.25 MHz KB-Aerotech Gamma transducers. The array is mounted on the wedge 218 at a 60° angle to thereby produce a 45° shear wave in the test specimen (e.g., a field coil) and minimize internal reflections. A cable 222 extends out of the transducer 216, connecting the transducer to a microprocessor controlled multiplexer (not shown). In accordance with the exemplary embodiment, a cast silicone rubber sock 224 having a tubular body 226 with openings 228 and 230 at opposite ends thereof provides the required acoustic coupling between the transducer and the test specimen. The sock 224 may be pulled over the transducer unit as shown in FIG. 3, with the sock closely adhering to the surface 220 and substantially enclosing the entire unit. Thus, one opening 228 lies on an end surface 232 of the transducer while the second opening 230 encloses tightly the cable 222. The sock or sleeve configuration for the acoustic coupling material enables the latter to be secured to the polymer (Plexiglas®) wedge 218 without the need for special fasteners or fixturing devices.

It should also be noted here that the wedge surface 220 is still polished to match the radius of curvature of the test specimen, in the principal direction of curvature. In other words, for a double curved surface, the wedge surface 220 would be curved in only one direction, with compliance assured via the silicone rubber sock 224.

The sock 224 is preferably formed of Dow Corning® HS II high strength moldmaking silicone rubber. The tensile and tear strengths of this material are 600 psi and 135 psi, respectively. The maximum elongation of the cured rubber is close to 500%. The sound velocity and density of the rubber are approximately 1,000 m/s and 1,200 kg/m$^3$ respectively. The Shore A Durometer hardness of the preferred silicone rubber is 16.

The wall thickness of the silicone rubber sock is approximately 2–10 mm and preferably 2–4 mm, depending on the required cushioning stiffness and mechanical stability. The stretched rubber sock lacks any sharp reflecting corners, and this "stealth technology" can lower the internal scattering noise of the probe by a factor of 5–10. Threshold sensitivity has been reduced to about 1–2%.

In addition, the sock provides excellent mechanical protection for the brittle wedge 218, the piezoelectric transducer 216 and especially the vulnerable connection between the cable 222 and the transducer 216.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An ultrasonic transducer for use in nondestructive testing comprising a multi-transducer array mounted on a wedge, said wedge including a sensing surface substantially contoured to conform to a surface to be tested wherein at least said sensing surface is partially covered by a tubular solid silicone rubber sock, and wherein said silicone rubber has the following properties:
    tensile strength—600 psi
    tear strength—135 psi
    sound velocity—1.000 m/s
    density—1,200 kg/m$^3$
    Shore A Durometer—16.

2. The ultrasonic transducer of claim 1 wherein said silicone rubber in a cured condition has a maximum elongation of about 500%.

3. The ultrasonic transducer of claim 1 wherein said sensing surface is contoured as a simple convex cylindrical surface.

4. The ultrasonic transducer of claim 1 wherein said sensing surface is contoured as a simple concave cylindrical surface.

5. The ultrasonic transducer of claim 1 wherein said sensing surface is contoured as a double curved surface.

6. The ultrasonic transducer of claim 1 wherein said silicone rubber encloses said array, said wedge and said sensing surface.

7. The ultrasonic transducer of claim 6 wherein said sock has a wall thickness of between about 2 and 10 mm.

8. An ultrasonic transducer for use in nondestructive testing comprising a multi-transducer array mounted on a wedge, said wedge including a sensing surface substantially contoured to conform to a surface to be tested wherein part of said sensing surface is covered by an open-ended silicone rubber sock, and further wherein said sock has front and rear openings, said front opening communicating with said sensing surface, and said rear opening accommodating one or more electrical cables, such that said multi-transducer array and said wedge are substantially enclosed within said sock.

9. The ultrasonic transducer of claim 8 wherein no fasteners are used to secure said sleeve.

10. The ultrasonic transducer of claim 9 wherein said silicon rubber sleeve has the following properties:
    tensile strength—600 psi
    tear strength—135 psi
    sound velocity—1,000 m/s
    density—1,200 kg/m$^3$
    Shore A Durometer—16.

11. The ultrasonic transducer of claim 8 wherein said silicone rubber sleeve in a cured condition has a maximum elongation of about 500%.

12. The ultrasonic transducer of claim 8 wherein said sensing surface is contoured as a simple convex cylindrical surface.

13. The ultrasonic transducer of claim 8 wherein said sensing surface is contoured as a simple concave cylindrical surface.

14. The ultrasonic transducer of claim 8 wherein said wedge is comprised of a polymer material.

15. The ultrasonic transducer of claim 8 wherein said sleeve has a wall thickness of between about 2 and 10 mm.

16. The ultrasonic transducer of claim 8 wherein said sleeve has a wall thickness of between about 2 and 4 mm.

* * * * *